US012566655B2

(12) United States Patent
Chen et al.

(10) Patent No.: US 12,566,655 B2
(45) Date of Patent: Mar. 3, 2026

(54) ANOMALY DETECTION USING METRIC TIME SERIES AND EVENT SEQUENCES FOR MEDICAL DECISION MAKING

(71) Applicant: NEC Laboratories America, Inc., Princeton, NJ (US)

(72) Inventors: Yuncong Chen, Plainsboro, NJ (US); LuAn Tang, Cranbury, NJ (US); Yanchi Liu, Monmouth Junction, NJ (US); Zhengzhang Chen, Princeton Junction, NJ (US); Haifeng Chen, West Windsor, NJ (US)

(73) Assignee: NEC Corporation, Tokyo (JP)

( * ) Notice: Subject to any disclaimer, the term of this patent is extended or adjusted under 35 U.S.C. 154(b) by 0 days.

(21) Appl. No.: 18/493,374

(22) Filed: Oct. 24, 2023

(65) Prior Publication Data

US 2024/0134736 A1 Apr. 25, 2024
US 2024/0231994 A9 Jul. 11, 2024

Related U.S. Application Data

(60) Provisional application No. 63/418,999, filed on Oct. 25, 2022.

(51) Int. Cl.
*G06F 11/07* (2006.01)
*G16H 50/20* (2018.01)

(52) U.S. Cl.
CPC ........ *G06F 11/079* (2013.01); *G06F 11/0709* (2013.01); *G06F 11/0793* (2013.01); *G16H 50/20* (2018.01)

(58) Field of Classification Search
CPC . G06F 11/079; G06F 11/0709; G06F 11/0793
See application file for complete search history.

(56) References Cited

U.S. PATENT DOCUMENTS

| | | | | | |
|---|---|---|---|---|---|
| 11,501,189 | B2 * | 11/2022 | Tiwari | ............... | H04L 63/1425 |
| 2020/0251213 | A1 * | 8/2020 | Tran | ...................... | G06N 20/00 |
| 2022/0179848 | A1 * | 6/2022 | Tran | ...................... | G06N 20/10 |
| 2022/0191113 | A1 * | 6/2022 | Oh | ......................... | H04L 43/062 |
| 2022/0284301 | A1 * | 9/2022 | Qiu | ...................... | G06N 3/0464 |
| 2023/0012236 | A1 * | 1/2023 | Cohn | ................... | G06N 3/0464 |

(Continued)

OTHER PUBLICATIONS

Shchur et al., "Intensity-Free Learning of Temporal Point Processes", arXiv:1909.12127v2 [cs.LG] Jan. 23, 2020, pp. 1-21.

(Continued)

*Primary Examiner* — Jigar P Patel

(74) *Attorney, Agent, or Firm* — Vincent Duffy; Joseph Kolodka

(57) ABSTRACT

Methods and systems for anomaly detection include encoding a multivariate time series and a multi-type event sequence using respective transformers and an aggregation network to generate a feature vector. Anomaly detection is performed using the feature vector to identify an anomaly within a system. A corrective action is performed responsive to the anomaly to correct or mitigate an effect of the anomaly. The detected anomaly can be used in a healthcare context to support decision making by medical professionals with respect to the treatment of a patient. The encoding may include machine learning models to implement the transformers and the aggregation network using deep learning.

19 Claims, 9 Drawing Sheets

(56)                References Cited

U.S. PATENT DOCUMENTS

2023/0021676 A1*  1/2023  Sreejith ................ G06V 10/764
2024/0135154 A1*  4/2024  Uniyal .................... G06N 3/08

OTHER PUBLICATIONS

Dubey et al., "Bayesian Neural Hawkes Process for Event Uncertainty Prediction", arXiv:2112.14474v2 [cs.LG] Jan. 19, 2022, pp. 1-13.

He et al., "Drain: An Online Log Parsing Approach with Fixed Depth Tree", In2017 IEEE international conference on web services (ICWS) Jun. 2, 2017, pp. 1-8.

Chen et al., "Forecast Oriented Classification of Spatio-Temporal Extreme Events", InTwenty-Third International Joint Conference on Artificial Intelligence Jun. 30, 2013, pp. 1-3.

Weiss et al., "Forest-Based Point Process for Event Prediction from Electronic Health Records", InMachine Learning and Knowledge Discovery in Databases: European Conference, ECML PKDD 2013, Prague, Czech Republic, Sep. 2013, pp. 1-16.

Zhou et al., "Neural Point Process for Learning Spatiotemporal Event Dynamics", arXiv:2112.06351v2 [cs.LG] May 20, 2022, pp. 1-21.

Chen et al., "Neural Spatio-Temporal Point Processes", arXiv:2011.04583v3 [cs.LG] Mar. 18, 2021, pp. 1-20.

Shchur et al., "Neural Temporal Point Processes: A Review", arXiv:2104.03528v5 [cs. LG] Aug. 25, 2021, pp. 1-9.

Omi et al., "Fully Neural Network based Model for General Temporal Point Processes", Advances in neural information processing systems, Dec. 2019, pp. 1-11.

Vaswani et al., "Attention Is All You Need", Advances in neural information processing systems, Dec. 2017, pp. 1-11.

Zuo et al., "Transformer Hawkes Process", InInternational conference on machine learning Nov. 21, 2020, pp. 1-11.

* cited by examiner

ANOMALY DETECTION USING METRIC TIME SERIES AND EVENT SEQUENCES FOR MEDICAL DECISION MAKING

RELATED APPLICATION INFORMATION

This application claims priority to U.S. patent application Ser. No. 63/418,999, filed on Oct. 25, 2022, incorporated herein by reference in its entirety.

BACKGROUND

Technical Field

The present invention relates to event prediction and, more particularly, to inferring system conditions from event history and time series information.

Description of the Related Art

Event prediction helps to manage complex systems. In cyber-physical systems, such as information technology systems, hardware failures may be predicted and preventative maintenance can be planned. In healthcare systems, adverse event prediction can help doctors adjust treatments early to prevent negative health outcomes.

SUMMARY

A method for anomaly detection includes encoding a multivariate time series and a multi-type event sequence using respective transformers and an aggregation network to generate a feature vector. Anomaly detection is performed using the feature vector to identify an anomaly within a system. A corrective action is performed responsive to the anomaly to correct or mitigate an effect of the anomaly.

A system for anomaly detection includes a hardware processor and a memory that stores a computer program. When executed by the hardware processor, the computer program causes the hardware processor to encode a multivariate time series and a multi-type event sequence using respective transformers and an aggregation network to generate a feature vector. Anomaly detection is performed using the feature vector to identify an anomaly within a system. A corrective action is performed responsive to the anomaly to correct or mitigate an effect of the anomaly.

A method for performing a treatment includes measuring time series information relating to a patient. The time series information and a health event sequence are encoded for the patient using respective transformers and an aggregation network to generate a feature vector. Anomaly detection is performed using the feature vector to identify health event. A corrective action is performed responsive to the health event to correct or mitigate a negative health effect of the health event.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein.

DETAILED DESCRIPTION OF PREFERRED EMBODIMENTS

Event prediction makes use of historical event information, but may also make use of information about system conditions that are constantly changing. System conditions can be inferred from current time series information about system metrics.

Events and time series information have complex causal interactions. For example, an increasing trend in memory usage in a computer system is likely to eventually cause an out-of-memory event. On the other hand, an elevated level of disk queue length can be the result of a disk-access—intensive application launch event. Event prediction that considers time series information as well as event history produces better outcomes than systems that consider either individually.

The measurements from the system may be correlated with the event logs, because many actions that cause changes in the measurements are recorded in the logs. For example, a sharp increase in processor usage may be expected if a large application is launched, but may be unusual if no such activities are recorded. On the other hand, a sudden burst of network traffic events is not abnormal if it is correlated with an increased number of users, but if the traffic measurements are normal, then the event burst may suggest a hardware failure. Furthermore, different metrics may be correlated with one another as they measure the same underlying performance factor. For example, both processor and memory usage reflect the level of system activity.

Furthermore, interpreting the system state may make use of the context given jointly by the time series of all metrics and the event logs. To make the detection result reliable and explainable, events responsive for a particular anomaly may be pinpointed.

Toward that end, a machine learning model can be used to predict the type and time of an anomaly, given a history of previous events and one or more time series metrics. Transformers and an attention mechanism are used to explicitly model the interaction between system events and metrics, encapsulating the interactions in hidden states. A support vector data description (SVDD) loss can be used to characterize encoded states of normal data and to detect whether incoming multivariate sensor data deviates from a normal state.

Figure 1:
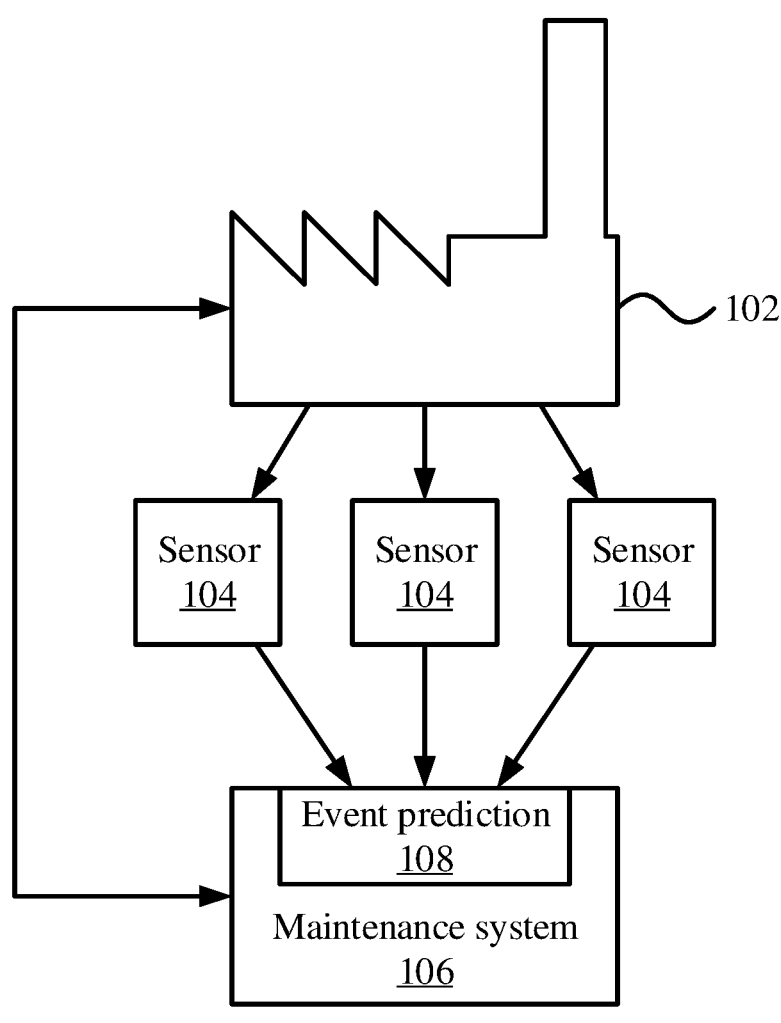
FIG. 1 is a diagram of a cyber-physical system that implements anomaly detection based on time series information and event log information, in accordance with an embodiment of the present invention.

Referring now to FIG. 1, a maintenance system 106 in the context of a monitored system 102 is shown. The monitored system 102 can be any appropriate system, including physical systems such as manufacturing lines and physical plant operations, electronic systems such as computers or other computerized devices, software systems such as operating systems and applications, and cyber-physical systems that combine physical systems with electronic systems and/or software systems. Exemplary systems 102 may include a wide range of different types, including railroad systems, power plants, vehicle sensors, data centers, and transportation systems.

One or more sensors 104 record information about the state of the monitored system 102. The sensors 104 can be any appropriate type of sensor including, for example, physical sensors, such as temperature, humidity, vibration, pressure, voltage, current, magnetic field, electrical field, and light sensors, and software sensors, such as logging utilities installed on a computer system to record information regarding the state and behavior of the operating system and applications running on the computer system. The information generated by the sensors 104 can be in any appropriate format and can include sensor log information generated with heterogeneous formats.

The sensors 104 may transmit the logged sensor information to an anomaly maintenance system 106 by any appropriate communications medium and protocol, including wireless and wired communications. The maintenance system 106 can, for example, identify abnormal or anomalous behavior by monitoring the multivariate time series that are generated by the sensors 104. Once anomalous behavior has been detected, the maintenance system 106 communicates with a system control unit to alter one or more parameters of the monitored system 102 to correct the anomalous behavior.

Exemplary corrective actions include changing a security setting for an application or hardware component, changing an operational parameter of an application or hardware component (for example, an operating speed), halting and/or restarting an application, halting and/or rebooting a hardware component, changing an environmental condition, changing a network interface's status or settings, etc. The maintenance system 106 thereby automatically corrects or mitigates the anomalous behavior. By identifying the particular sensors 104 that are associated with the anomalous classification, the amount of time needed to isolate a problem can be decreased.

Each of the sensors 104 outputs a respective time series, which encodes measurements made by the sensor over time. For example, the time series may include pairs of information, with each pair including a measurement and a time-stamp, representing the time at which the measurement was made. Each time series may be divided into segments, which represent measurements made by the sensor over a particular time range. Time series segments may represent any appropriate interval, such as one second, one minute, one hour, or one day. Time series segments may represent a set number of collection time points, rather than a fixed period of time, for example covering 100 measurements.

The maintenance system 106 may track occurrences of events relating to the condition of the monitored system 102. For example, the maintenance system 106 may receive information relating to workload, starting and stopping of jobs, and malfunctions. This information may be recorded with appropriate time-stamp and other condition information relating to the state of the monitored system 102 at the time the event occurred, for example including information collected by the sensors 104. Whereas time series information may be recorded periodically or on an aperiodic but frequent basis, the event information may be recorded whenever a discrete event occurs.

The maintenance system 106 may predict when a future event occur using event prediction 108. The event prediction makes use of both the event history information and the time series information to determine when an event is likely to occur. The maintenance system 106 can furthermore determine which source(s) of information contribute most to the prediction, so that a corrective action taken by the maintenance system 106 can be tailored to a root cause of a problem.

Figure 2:
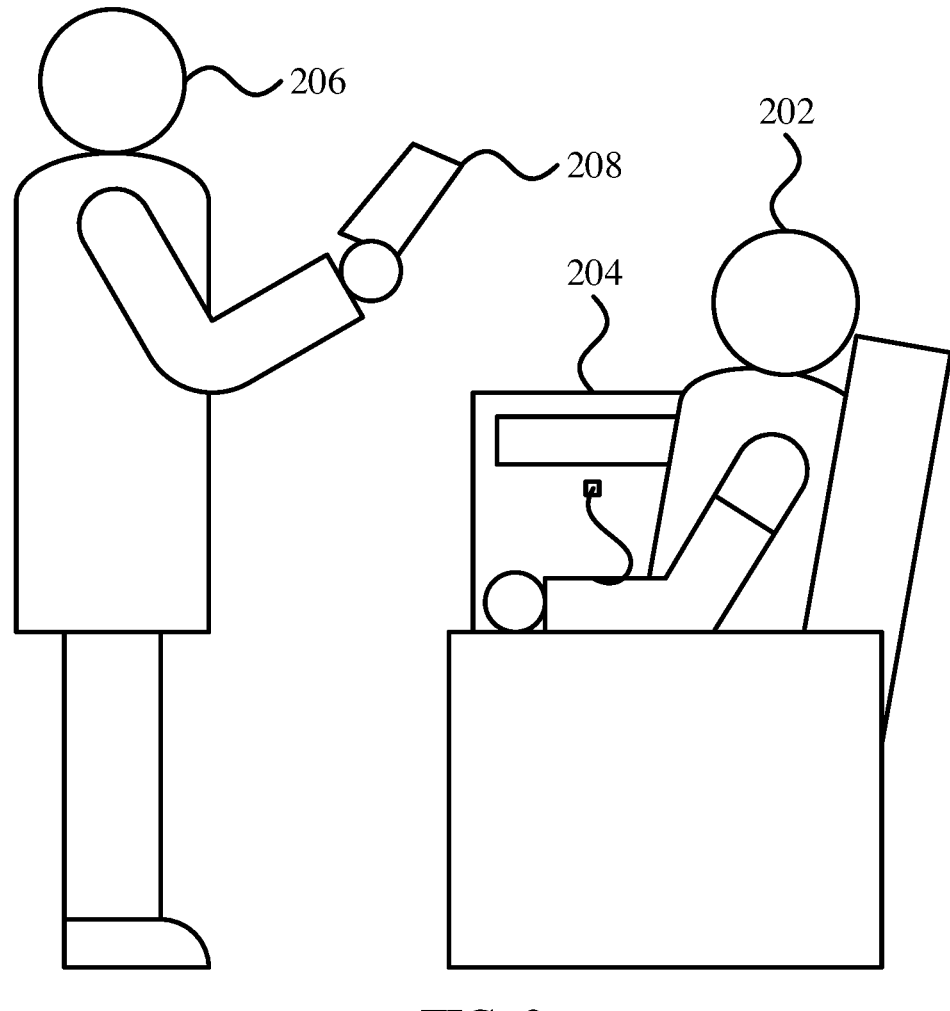
FIG. 2 is a diagram of a patient in a healthcare context receiving treatment in accordance with a detected health anomaly, in accordance with an embodiment of the present invention.

Referring now to FIG. 2, patient 20 is shown in the context of a healthcare system. For example, the patient 202 may be in a hemodialysis (also known simply as "dialysis") session. During dialysis, a dialysis machine 204 automatically draws the patient's blood, processes and purifies the blood, and then reintroduces the purified blood to the patient's body. Dialysis can take as long as four hours to complete, and may be performed every three days, though other durations and periods are contemplated. Although dialysis is specifically contemplated, it should be understood that any appropriate medical procedure, monitoring, or system may be used instead.

Before, during, and after a dialysis session, a patient 202 may experience a health event relating to the treatment. Such health events can be dangerous to the patient 202, but can be predicted based on knowledge of previous health events and the patient's present health metrics. Before the patient 202 undergoes a medical procedure or treatment, such as dialysis, a medical professional 206 reviews a recommendation 208 that includes a prediction score. This prediction score indicates a likelihood that a health event will occur during the dialysis session. The recommendation 208 may furthermore include information relating to the type of event that is predicted, as well as measurements of the patient's status It is specifically contemplated that this recommendation may be made before the dialysis session begins, so that treatment can be adjusted.

The recommendation may be made based on a variety of input information. Part of that information includes a static profile of the patient, for example including information such as age, sex, starting time of dialysis, previous health events, etc. The information also includes dynamic data, such as dialysis measurement records, which may be taken at every dialysis session, blood pressure, weight, venous pressure, blood test measurements, and cardiothoracic ratio (CTR). The blood test measurements may be taken regularly, for example at a frequency of twice per month, and may measure such factors as albumin, glucose, and platelet count. The CTR may also be taken regularly, for example at a frequency of once per month. Dynamic information may also be recorded during the dialysis session, for example using sensors in the dialysis machine 204. The dynamic information may be modeled as time series over their respective frequencies.

In addition, the systems themselves may be monitored within a healthcare environment. For example, operational parameters of a dialysis machine 204 or any other system in a hospital or other healthcare facility many be monitored, along with a history of past events at the system, to detect anomalies as described below. When an anomaly is detected, a corrective action may be performed and/or a system administrator may be notified.

Figure 3:
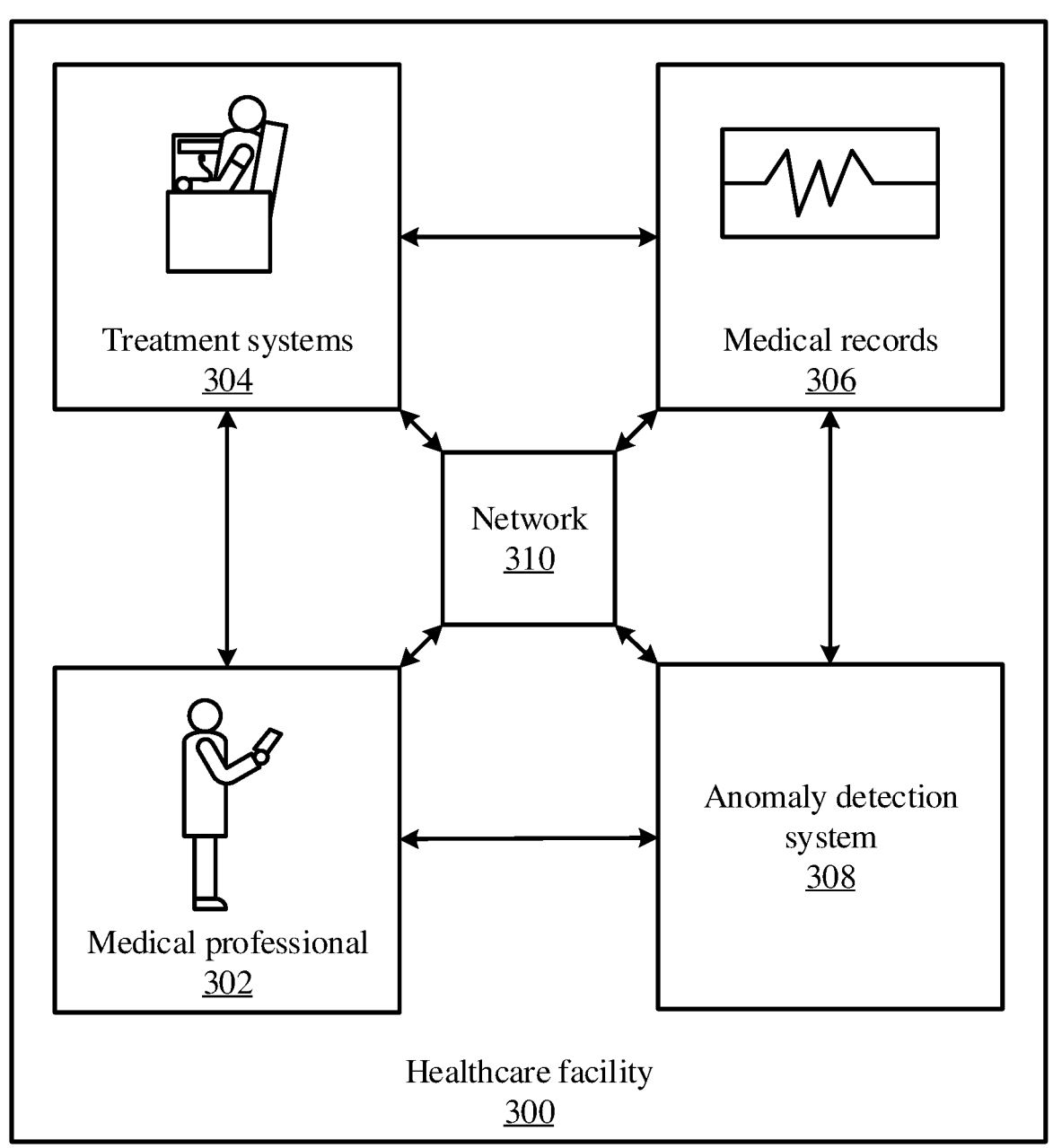
FIG. 3 is a block diagram of a healthcare facility where information on the functioning of treatment systems and medical records are used to detect anomalies, in accordance with an embodiment of the p resent invention.

Referring now to FIG. 3, a diagram of anomaly detection in the context of a healthcare facility 300. Rather than, or in addition to, detecting anomalies in the context of a single patient's treatments, the present principles may be applied to all of the systems within the facility. This may be used to help monitor and treat multiple patients, for example responding to changes in environmental conditions and shortages of materials. Such facilities may also be vulnerable to cyber-attack, and detecting anomalies in such a context can help to identify and stop the attack, preserving the facility's ability to treat patients.

The healthcare facility may include one or more medical professionals 302 who provide information relating to anomalies and measurements of system status to an anomaly detection system 308. Treatment systems 304 may furthermore monitor patient status to generate medical records 306 and may be designed to automatically administer and adjust treatments as needed.

Based on information drawn from at least the medical professionals 302, treatment systems 304, and medical records 306, anomaly detection system 308 can detect anomalies and can automatically respond to correct or mitigate the detected anomalies. For example, corrective action can be taken and/or facility administrators may be notified. In the event that an administrator is notified, the anomaly detection can be used to support decision-making by the hospital's administrator.

The different elements of the healthcare facility 300 may communicate with one another via a network 310, for example using any appropriate wired or wireless communications protocol and medium. Thus the output of the anomaly detection system 308 may access remotely stored medical records 306, may communicate with the treatment systems 304, and may receive instructions and send reports to medical professionals 302.

Figure 4:
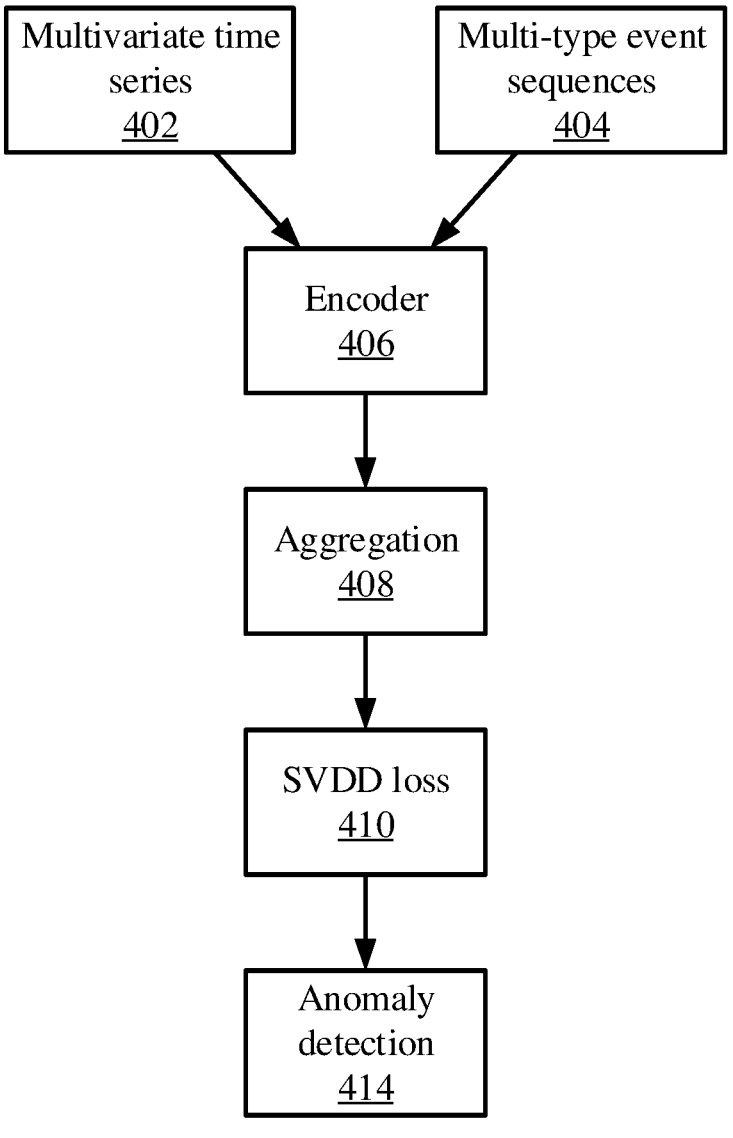
FIG. 4 is a block/flow diagram of an anomaly detection method/system, in accordance with an embodiment of the present invention.

Referring now to FIG. 4, anomaly detection using time series information and event sequence information is shown. The input may include multivariate time series 402, for example combining multiple time series from different respective sensors. The input may further include multi-type event sequences 404, which may indicate a type of event, a time that the event occurred, and any other appropriate information relating to the event. The multi-type event sequences may include multiple distinct types of event.

An encoder 406 embeds the inputs into a latent space, generating a set of features that represent the joint inputs 402 and 404. Each input may generate a respective feature vector, and these vectors may be aggregated together 408 to create a context vector. The encoder(s) 406 may include transformers with stacks of self-attention and cross-attention layers that fuse the information among different time steps from each sequence. The hidden states from each time step of each sequence are then concatenated and passed to the aggregator network. 408. The aggregator network 408 may include self-attention layers that fuse the information from all time steps of both streams and outputs a context vector.

The context vector may be used as an input to an SVDD loss function 410. Feature vectors from all the training data may be used to compute the SVDD loss 410, which may be interpreted as the radius of a minimal hypersphere that encompasses all training data in a latent feature space. The output of the SVDD loss function 410 may be used to detect anomalies 414.

Figure 5:
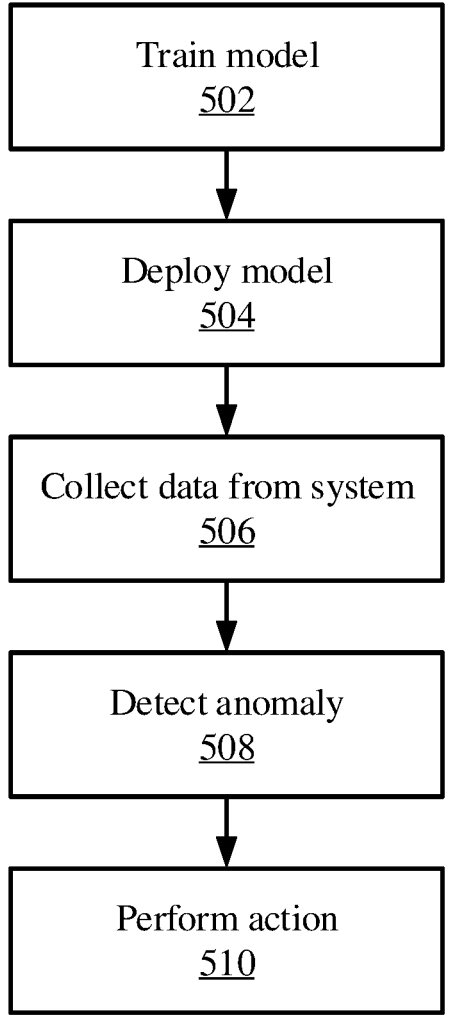
FIG. 5 is a block/flow diagram of a method for training and using a deep learning model for anomaly detection, in accordance with an embodiment of the present invention.

Referring now to FIG. 5, a method for detecting and addressing anomalies is shown. Block 502 acquires a set of training data, which may include system metric time series and timestamped event sequences, and trains a machine learning model, as will be described in greater detail below, to detect anomalies. The training process 502 may use multivariate time series and event logs collected during normal operating conditions of a system and may use this information to optimize according to the SVDD loss 410. The trained model is then deployed 504 to an installation, for example in the management system 106 of a cyber-physical system or a healthcare analytics system.

New data may be collected from the installation, including event information and multivariate time series information, at block 506. This new data represents the operational state of the system and its particular event history. The trained model is used in block 508 to generate an anomaly score relating to the operation of the system, for example with an above-threshold anomaly score being interpreted as an anomalous operational state. If the anomaly score is higher than the threshold, block 508 may further generate a ranked list of system events that are potential causes of the anomaly. For example, this event prediction may relate to an expected system malfunction or adverse health event.

Block 510 then performs an action to prevent or mitigate the harm of the predicted event. In the context of cyber-physical system 102, the action may include performing an automated response that addresses one or more sub-systems that are expected to be related to the predicted event. For example, the action may include changing an environmental parameter to prevent overheating or may shut down a sub-system to prevent damage.

In the context of a patient 202, where the detected anomaly is an adverse health event, the action may include an automatic adjustment to a treatment, for example adjusting the operation of a dialysis machine 204, adjusting dosage of an intravenously administered drug, or halting a treatment that is deemed to be dangerous.

Figure 6:
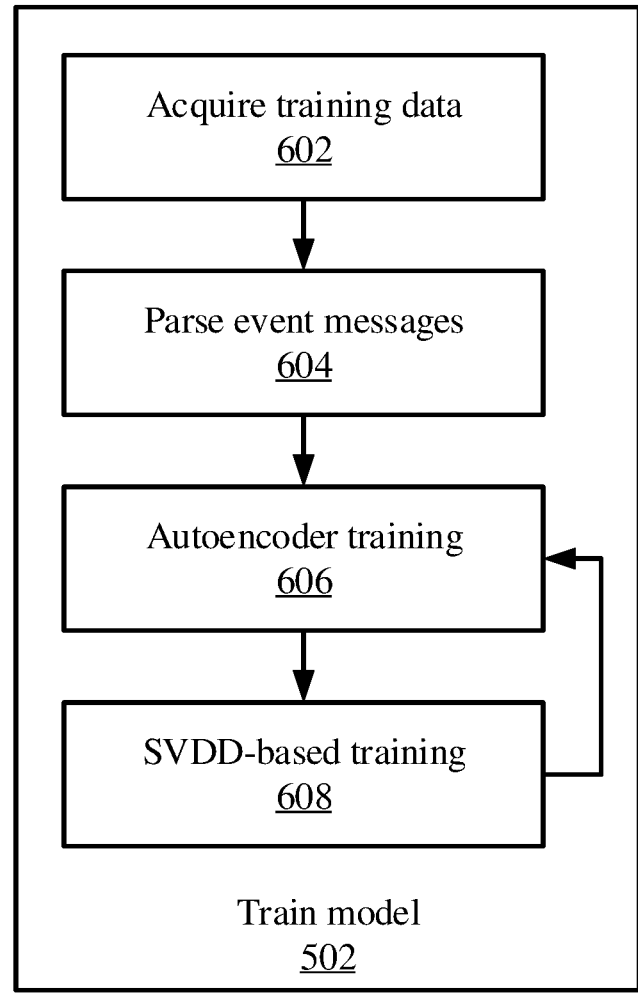
FIG. 6 is a block/flow diagram of a method of training a deep learning model to detect anomalies, in accordance with an embodiment of the present invention.

Referring now to FIG. 6, additional detail on training 502 is shown. Block 602 acquires a set of training data, including synchronized system metric time series and timestamped system event sequences. Block 604 parses the event messages in the system event sequences to identify the event type from each message, for example representing each distinct type of event as a different integer value.

The training data may be split into context windows, for example using overlapping windows of a fixed length. Each training sample may come from a respective time window, including the time series segment $x_i$ in the window, the event subsequence $v_i$ in the window, and the event (type $u_i$ at time $t_i$) that follows immediately after the window.

Training may be performed in two phases. In a first phase, autoencoder training 606 may be performed, as will be described in greater detail below. The autoencoder training 606 trains an encoder to determine hidden states of an input time series and uses a decoder to reconstitute the input time series. An autoencoder loss is used to update parameters of the autoencoder, for example using a stochastic gradient descent. The encoder part of the autoencoder may be used in encoder 406.

In a second phase, the entire model is trained using an SVDD loss, as will be described in greater detail below. The encoder 406 and the aggregation network 408 are used to generate a feature vector for a training example and an SVDD loss is computed. Based on the SVDD loss, the parameters of the encoder 406 and the aggregation network 408 may be adjusted according to, e.g., a stochastic gradient descent.

The multivariate time series may first be processed by a one-dimensional convolutional layer, with the result at each timestamp being concatenated with the corresponding time embedding vector before being input to the encoder 406. Event sequences may be first parsed by a log parser to decompose each event message into a template and parameters. For example, the message, "ESMCommonService has transitioned to the stopped state," may be converted to a template, "[*] has transitioned to the stopped state," and the parameters, "ESMCommonService." A template type embedding layer and a parameter embedding layer are learned to convert the template type and parameters to vectors, respectively. For each event in the sequence, the template type embedding vector, the parameter embedding vector, and the time embedding vector are concatenated and used as input to the transformer encoder.

The aggregation network 408 is a stack of self-attention layers. The hidden state of the time series transformer encoder at the last timestep may be used to compute a latent vector h. The latent vector h is then used as a condition and the initial Gidden state for a gated recurrent unit (GRU) decoder. The GRU decoder outputs a time series having the same length as the input time series. The encoder 406 and the decoder may be trained together in block 606 to minimize the autoencoder error between the input time series and the decoder's output.

In the second training phase 608, the feature vector $x_i$ from the aggregation network 408 is used to compute the SVDD loss:

$$\mathcal{L} = \frac{1}{n}\sum_{i=1}^{n}\|\phi(x_i; W) - c\|^2 + \frac{\lambda}{2}\|W\|_F^2$$

where $\phi$ is an encoder network including the transformers and aggregation network, W are neural network parameters, c is a hypersphere in feature space, and A is a hyperparameter. A randomly sampled batch of values may be sampled from a training dataset and the mean of the resulting feature vectors may be determined to generate c. The first term of the loss is the radius of the hypersphere that encompasses all n training data values in the feature space. The second term regularizes the magnitude of the network parameters. The loss may be minimized by adjusting the parameters W using, e.g., a stochastic gradient descent.

After the model is trained and deployed, at a time t, the events and time series in a fixed-size context window preceding t may be input to the model. The model outputs an anomaly score, for example by calculating the SVDD loss. System events having the highest attention weights (e.g., selecting the top k weights) may be output as potential causes in the event that the anomaly score exceeds a threshold value.

Figure 7:
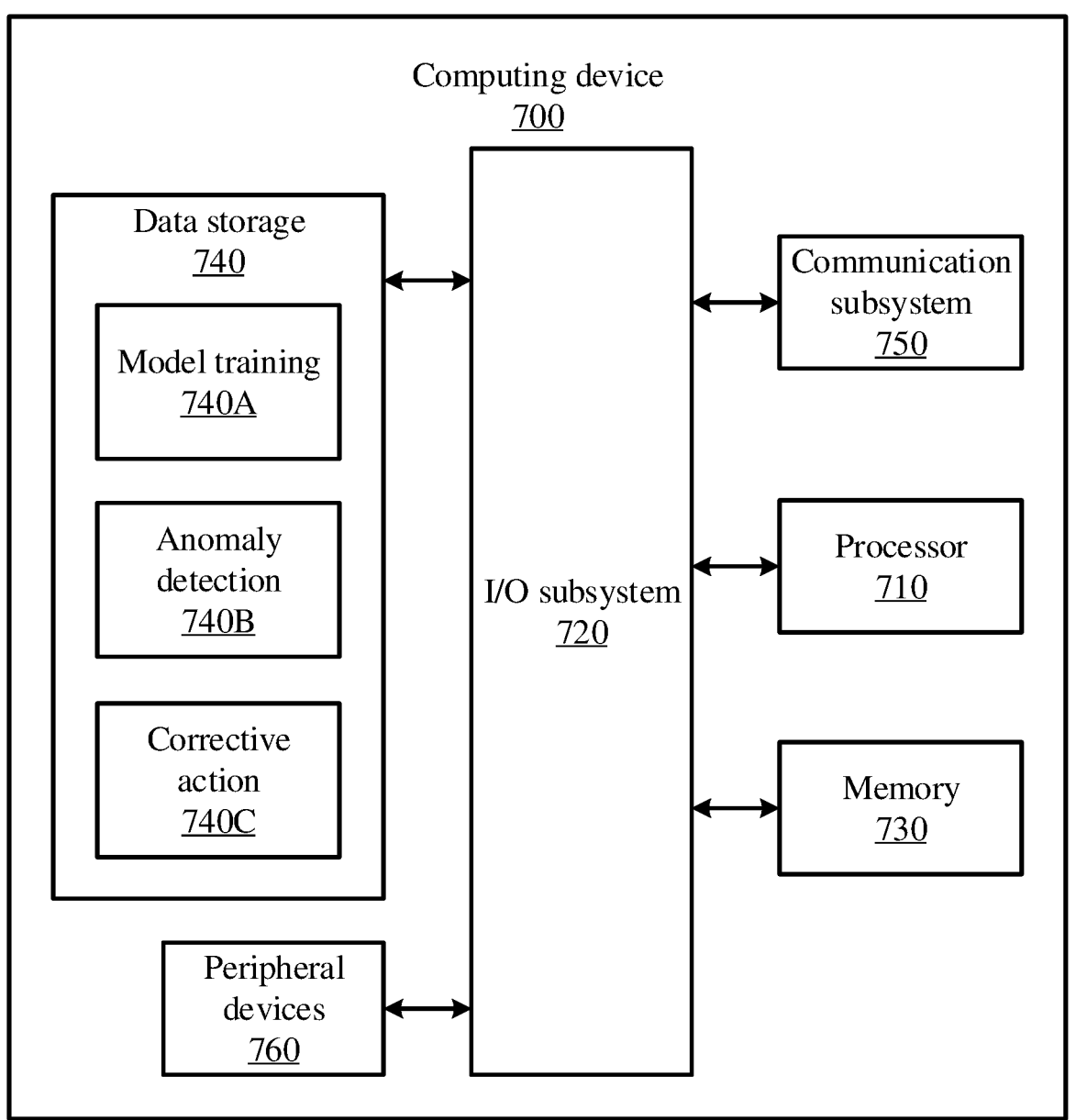
FIG. 7 is a block diagram of a computing device that can train and use an event prediction model to detect and correct anomalies, in accordance with an embodiment of the present invention.

Referring now to FIG. 7, an exemplary computing device 700 is shown, in accordance with an embodiment of the present invention. The computing device 700 is configured to perform anomaly detection.

The computing device 700 may be embodied as any type of computation or computer device capable of performing the functions described herein, including, without limitation, a computer, a server, a rack based server, a blade server, a workstation, a desktop computer, a laptop computer, a notebook computer, a tablet computer, a mobile computing device, a wearable computing device, a network appliance, a web appliance, a distributed computing system, a processor-based system, and/or a consumer electronic device. Additionally or alternatively, the computing device 700 may be embodied as one or more compute sleds, memory sleds, or other racks, sleds, computing chassis, or other components of a physically disaggregated computing device.

As shown in FIG. 7, the computing device 700 illustratively includes the processor 710, an input/output subsystem 720, a memory 730, a data storage device 740, and a communication subsystem 750, and/or other components and devices commonly found in a server or similar computing device. The computing device 700 may include other or additional components, such as those commonly found in a server computer (e.g., various input/output devices), in other embodiments. Additionally, in some embodiments, one or more of the illustrative components may be incorporated in, or otherwise form a portion of, another component. For example, the memory 730, or portions thereof, may be incorporated in the processor 710 in some embodiments.

The processor 710 may be embodied as any type of processor capable of performing the functions described herein. The processor 710 may be embodied as a single processor, multiple processors, a Central Processing Unit(s) (CPU(s)), a Graphics Processing Unit(s) (GPU(s)), a single or multi-core processor(s), a digital signal processor(s), a microcontroller(s), or other processor(s) or processing/controlling circuit(s).

The memory 730 may be embodied as any type of volatile or non-volatile memory or data storage capable of performing the functions described herein. In operation, the memory 730 may store various data and software used during operation of the computing device 700, such as operating systems, applications, programs, libraries, and drivers. The memory 730 is communicatively coupled to the processor 710 via the I/O subsystem 720, which may be embodied as circuitry and/or components to facilitate input/output operations with the processor 710, the memory 730, and other components of the computing device 700. For example, the I/O subsystem 720 may be embodied as, or otherwise include, memory controller hubs, input/output control hubs, platform controller hubs, integrated control circuitry, firmware devices, communication links (e.g., point-to-point links, bus links, wires, cables, light guides, printed circuit board traces, etc.), and/or other components and subsystems to facilitate the input/output operations. In some embodiments, the I/O subsystem 720 may form a portion of a system-on-a-chip (SOC) and be incorporated, along with the processor 710, the memory 730, and other components of the computing device 700, on a single integrated circuit chip.

The data storage device 740 may be embodied as any type of device or devices configured for short-term or long-term storage of data such as, for example, memory devices and circuits, memory cards, hard disk drives, solid state drives, or other data storage devices. The data storage device 740 can store program code 740A for training a model, 740B for detecting an anomaly, and/or 740C for performing a corrective action responsive to the detected anomaly. Any or all of these program code blocks may be included in a given computing system. The communication subsystem 750 of the computing device 700 may be embodied as any network interface controller or other communication circuit, device, or collection thereof, capable of enabling communications between the computing device 700 and other remote devices over a network. The communication subsystem 750 may be configured to use any one or more communication technology (e.g., wired or wireless communications) and associated protocols (e.g., Ethernet, InfiniBand®, Bluetooth®, Wi-Fi®, WiMAX, etc.) to effect such communication.

As shown, the computing device 700 may also include one or more peripheral devices 760. The peripheral devices 760 may include any number of additional input/output devices, interface devices, and/or other peripheral devices. For example, in some embodiments, the peripheral devices 760 may include a display, touch screen, graphics circuitry, keyboard, mouse, speaker system, microphone, network interface, and/or other input/output devices, interface devices, and/or peripheral devices.

Of course, the computing device 700 may also include other elements (not shown), as readily contemplated by one of skill in the art, as well as omit certain elements. For example, various other sensors, input devices, and/or output devices can be included in computing device 700, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized. These and other variations of the processing system 700 are readily contemplated by one of ordinary skill in the art given the teachings of the present invention provided herein.

Figure 8:
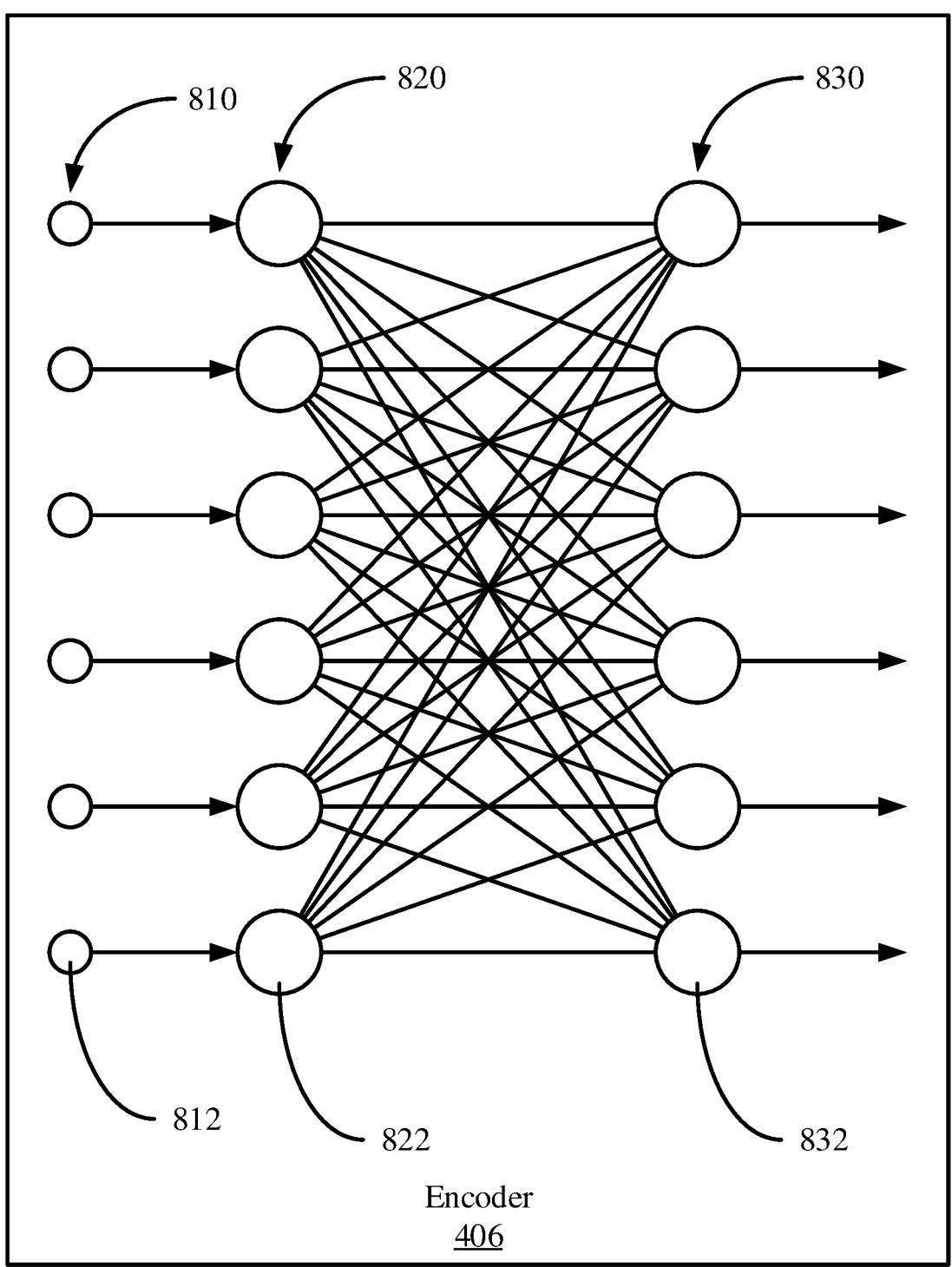
FIG. 8 is a diagram of an exemplary neural network architecture that may be used to implement part of an anomaly prediction model, in accordance with an embodiment of the present invention.
Figure 9:
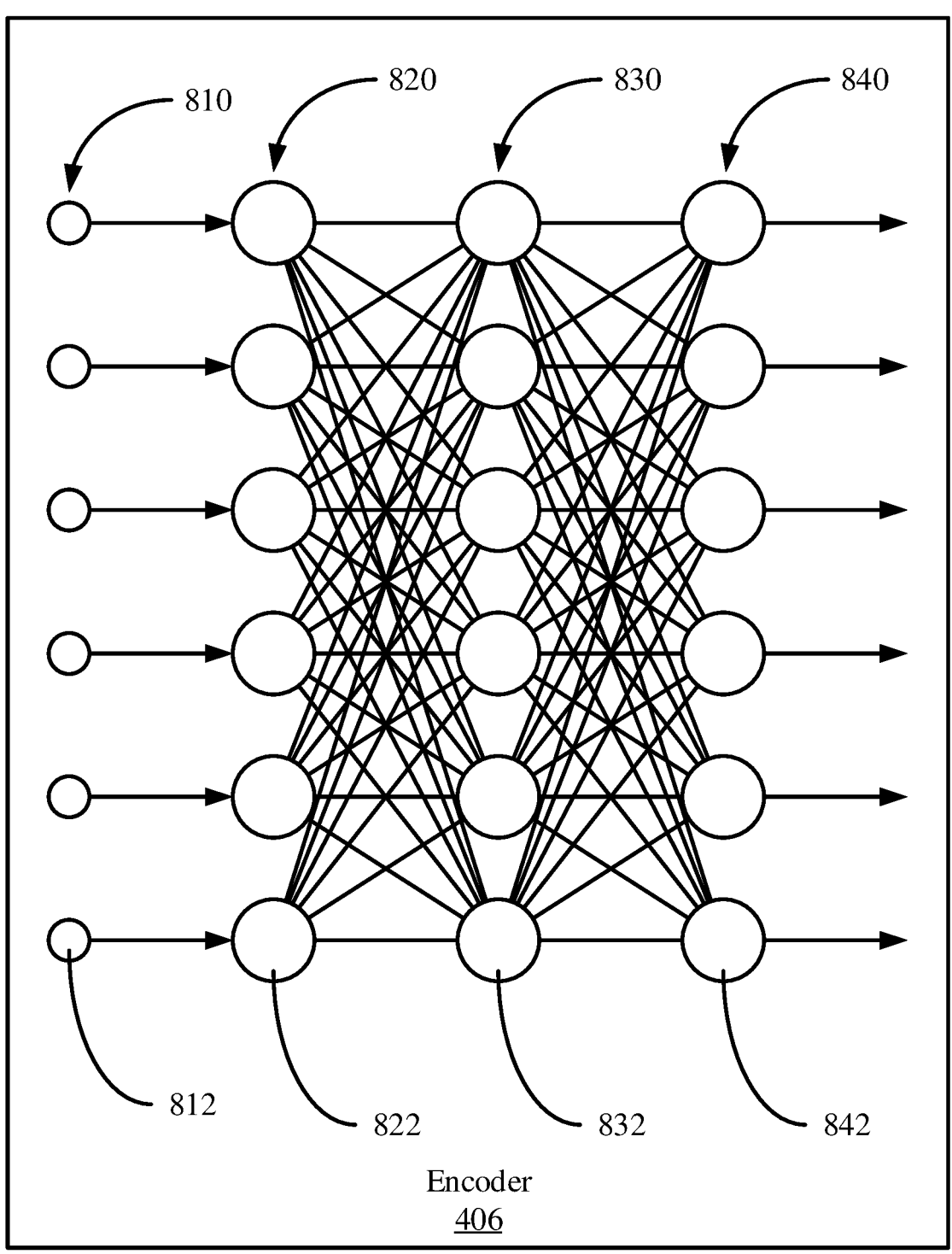
FIG. 9 is a diagram of an exemplary deep neural network architecture that may be used to implement part of an anomaly prediction model, in accordance with an embodiment of the present invention.

Referring now to FIGS. 8 and 9, exemplary neural network architectures are shown, which may be used to implement parts of the present models, such as the encoder 406. A neural network is a generalized system that improves its functioning and accuracy through exposure to additional empirical data. The neural network becomes trained by exposure to the empirical data. During training, the neural network stores and adjusts a plurality of weights that are applied to the incoming empirical data. By applying the adjusted weights to the data, the data can be identified as belonging to a particular predefined class from a set of classes or a probability that the input data belongs to each of the classes can be output.

The empirical data, also known as training data, from a set of examples can be formatted as a string of values and fed into the input of the neural network. Each example may be associated with a known result or output. Each example can be represented as a pair, (x, y), where x represents the input data and y represents the known output. The input data may include a variety of different data types, and may include multiple distinct values. The network can have one input node for each value making up the example's input data, and a separate weight can be applied to each input value. The input data can, for example, be formatted as a vector, an array, or a string depending on the architecture of the neural network being constructed and trained.

The neural network "learns" by comparing the neural network output generated from the input data to the known values of the examples, and adjusting the stored weights to minimize the differences between the output values and the known values. The adjustments may be made to the stored weights through back propagation, where the effect of the weights on the output values may be determined by calculating the mathematical gradient and adjusting the weights in a manner that shifts the output towards a minimum difference. This optimization, referred to as a gradient descent approach, is a non-limiting example of how training may be performed. A subset of examples with known values that were not used for training can be used to test and validate the accuracy of the neural network.

During operation, the trained neural network can be used on new data that was not previously used in training or validation through generalization. The adjusted weights of the neural network can be applied to the new data, where the weights estimate a function developed from the training examples. The parameters of the estimated function which are captured by the weights are based on statistical inference.

In layered neural networks, nodes are arranged in the form of layers. An exemplary simple neural network has an input layer 820 of source nodes 822, and a single computation layer 830 having one or more computation nodes 832 that also act as output nodes, where there is a single computation node 832 for each possible category into which the input example could be classified. An input layer 820 can have a number of source nodes 822 equal to the number of data values 812 in the input data 810. The data values 812 in the input data 810 can be represented as a column vector. Each computation node 832 in the computation layer 830 generates a linear combination of weighted values from the input data 810 fed into input nodes 820, and applies a non-linear activation function that is differentiable to the sum. The exemplary simple neural network can perform classification on linearly separable examples (e.g., patterns).

A deep neural network, such as a multilayer perceptron, can have an input layer 820 of source nodes 822, one or more computation layer(s) 830 having one or more computation nodes 832, and an output layer 840, where there is a single output node 842 for each possible category into which the input example could be classified. An input layer 820 can have a number of source nodes 822 equal to the number of data values 812 in the input data 810. The computation nodes 832 in the computation layer(s) 830 can also be referred to as hidden layers, because they are between the source nodes 822 and output node(s) 842 and are not directly observed. Each node 832, 842 in a computation layer generates a linear combination of weighted values from the values output from the nodes in a previous layer, and applies a non-linear activation function that is differentiable over the range of the linear combination. The weights applied to the value from each previous node can be denoted, for example, by $w_1, w_2, \ldots w_{n-1}, w_n$. The output layer provides the overall response of the network to the input data. A deep neural network can be fully connected, where each node in a computational layer is connected to all other nodes in the previous layer, or may have other configurations of connections between layers. If links between nodes are missing, the network is referred to as partially connected.

Training a deep neural network can involve two phases, a forward phase where the weights of each node are fixed and the input propagates through the network, and a backwards phase where an error value is propagated backwards through the network and weight values are updated.

The computation nodes 832 in the one or more computation (hidden) layer(s) 830 perform a nonlinear transformation on the input data 812 that generates a feature space. The classes or categories may be more easily separated in the feature space than in the original data space.

Embodiments described herein may be entirely hardware, entirely software or including both hardware and software elements. In a preferred embodiment, the present invention is implemented in software, which includes but is not limited to firmware, resident software, microcode, etc.

Embodiments may include a computer program product accessible from a computer-usable or computer-readable medium providing program code for use by or in connection with a computer or any instruction execution system. A computer-usable or computer readable medium may include any apparatus that stores, communicates, propagates, or transports the program for use by or in connection with the instruction execution system, apparatus, or device. The medium can be magnetic, optical, electronic, electromagnetic, infrared, or semiconductor system (or apparatus or device) or a propagation medium. The medium may include a computer-readable storage medium such as a semiconductor or solid state memory, magnetic tape, a removable computer diskette, a random access memory (RAM), a read-only memory (ROM), a rigid magnetic disk and an optical disk, etc.

Each computer program may be tangibly stored in a machine-readable storage media or device (e.g., program memory or magnetic disk) readable by a general or special purpose programmable computer, for configuring and controlling operation of a computer when the storage media or device is read by the computer to perform the procedures described herein. The inventive system may also be considered to be embodied in a computer-readable storage medium, configured with a computer program, where the storage medium so configured causes a computer to operate in a specific and predefined manner to perform the functions described herein.

A data processing system suitable for storing and/or executing program code may include at least one processor coupled directly or indirectly to memory elements through a system bus. The memory elements can include local memory employed during actual execution of the program code, bulk storage, and cache memories which provide temporary storage of at least some program code to reduce the number of times code is retrieved from bulk storage during execution. Input/output or I/O devices (including but not limited to keyboards, displays, pointing devices, etc.) may be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

As employed herein, the term "hardware processor subsystem" or "hardware processor" can refer to a processor, memory, software or combinations thereof that cooperate to perform one or more specific tasks. In useful embodiments, the hardware processor subsystem can include one or more data processing elements (e.g., logic circuits, processing circuits, instruction execution devices, etc.). The one or more data processing elements can be included in a central processing unit, a graphics processing unit, and/or a separate processor- or computing element-based controller (e.g., logic gates, etc.). The hardware processor subsystem can include one or more on-board memories (e.g., caches, dedicated memory arrays, read only memory, etc.). In some embodiments, the hardware processor subsystem can include one or more memories that can be on or off board or that can be dedicated for use by the hardware processor subsystem (e.g., ROM, RAM, basic input/output system (BIOS), etc.).

In some embodiments, the hardware processor subsystem can include and execute one or more software elements. The one or more software elements can include an operating system and/or one or more applications and/or specific code to achieve a specified result.

In other embodiments, the hardware processor subsystem can include dedicated, specialized circuitry that performs one or more electronic processing functions to achieve a specified result. Such circuitry can include one or more application-specific integrated circuits (ASICs), field-programmable gate arrays (FPGAs), and/or programmable logic arrays (PLAs).

These and other variations of a hardware processor subsystem are also contemplated in accordance with embodiments of the present invention.

Reference in the specification to "one embodiment" or "an embodiment" of the present invention, as well as other variations thereof, means that a particular feature, structure, characteristic, and so forth described in connection with the embodiment is included in at least one embodiment of the present invention. Thus, the appearances of the phrase "in one embodiment" or "in an embodiment", as well any other variations, appearing in various places throughout the specification are not necessarily all referring to the same embodiment. However, it is to be appreciated that features of one or more embodiments can be combined given the teachings of the present invention provided herein.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended for as many items listed.

The foregoing is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the present invention and that those skilled in the art may implement various modifications without departing from the scope and spirit of the invention. Those skilled in the art could implement various other feature combinations without departing from the scope and spirit of the invention. Having thus described aspects of the invention, with the details and particularity required by the patent laws, what is claimed and desired protected by Letters Patent is set forth in the appended claims.

What is claimed is:

1. A computer-implemented method for anomaly detection, comprising:

encoding a multivariate time series and a multi-type event sequence using respective transformers and an aggregation network to generate a feature vector;

performing anomaly detection by determining an anomaly score with a support vector data description (SVDD) loss using the feature vector to identify an anomaly within a system, the SVDD lost being determined as:

$$\mathcal{L} = \frac{1}{n}\sum_{i=1}^{n}\|\phi(x_i; W) - c\|^2 + \frac{\lambda}{2}\|W\|_F^2$$

where $x_i$ is the feature vector, n is a number of training values, $\phi$ is an encoder network including the transformers and aggregation network, W are neural network parameters, c is a hypersphere in feature space, and $\lambda$ is a hyperparameter; and performing a corrective action responsive to the anomaly to correct or mitigate an effect of the anomaly.

2. The method of claim 1, wherein performing anomaly detection uses support vector data description that includes a hypersphere radius term and a network parameter regularization term.

3. The method of claim 2, wherein the hypersphere radius term represents a radius of a hypersphere that encompasses input multivariate time series data in a feature space.

4. The method of claim 1, wherein the aggregation network includes a stack of self-attention layers that convert outputs of the respective transformers to the feature vector.

5. The method of claim 1, further determining a ranked list of past events and time series measurements that most influence the anomaly.

6. The method of claim 5, wherein determining the ranked list is performed according to attention weights from the aggregation network.

7. The method of claim 1, wherein the transformers and the aggregation network are trained using deep learning, with a set of training data that includes synchronized time series information and timestamped event sequences.

8. The method of claim 1, further comprising reporting the detected anomaly to a medical professional to support medical decision-making.

9. The method of claim 1, wherein performing the corrective action includes an action selected from the group consisting of changing a security setting for an application or hardware component, changing an operational parameter of an application or hardware component, halting and/or restarting an application, halting and/or rebooting a hardware component, changing an environmental condition, and changing a network interface's status or settings.

10. A system for anomaly detection, comprising:
a hardware processor; and
a memory that stores a computer program which, when executed by the hardware processor, causes the hardware processor to:
encode a multivariate time series and a multi-type event sequence using respective transformers and an aggregation network to generate a feature vector;
perform anomaly detection by determining an anomaly score with a support vector data description (SVDD) loss using the feature vector to identify an anomaly within a system, the SVDD lost being determined as:

$$\mathcal{L} = \frac{1}{n}\sum_{i=1}^{n}\|\phi(x_i; W) - c\|^2 + \frac{\lambda}{2}\|W\|_F^2$$

where $x_i$ is the feature vector, n is a number of training values, $\phi$ is an encoder network including the transformers and aggregation network, W are neural network parameters, c is a hypersphere in feature space, and $\lambda$ is a hyperparameter; and
perform a corrective action responsive to the anomaly to correct or mitigate an effect of the anomaly.

11. The system of claim 10, wherein the computer program causes the hardware processor to support vector data description that includes a hypersphere radius term and a network parameter regularization term for anomaly detection.

12. The system of claim 11, wherein the hypersphere radius term represents a radius of a hypersphere that encompasses input multivariate time series data in a feature space.

13. The system of claim 10, wherein the computer program further causes the hardware processor to determine an anomaly score and to compare the anomaly score to a threshold, where an above-threshold anomaly score indicates an anomaly.

14. The system of claim 10, wherein the aggregation network includes a stack of self-attention layers that convert outputs of the respective transformers to the feature vector.

15. The system of claim 10, wherein the computer program further causes the hardware processor to determine a ranked list of past events and time series measurements that most influence the anomaly.

16. The system of claim 15, wherein the determination of the ranked list is performed according to attention weights from the aggregation network.

17. The system of claim 10, wherein the corrective action includes an action selected from the group consisting of changing a security setting for an application or hardware component, changing an operational parameter of an application or hardware component, halting and/or restarting an application, halting and/or rebooting a hardware component, changing an environmental condition, and changing a network interface's status or settings.

18. A method for performing a treatment, comprising:
measuring time series information relating to a patient;
encoding the time series information and a health event sequence for the patient using respective transformers and an aggregation network to generate a feature vector;
performing anomaly detection by determining an anomaly score with a support vector data description (SVDD) loss using the feature vector to identify health event, the SVDD lost being determined as:

$$\mathcal{L} = \frac{1}{n}\sum_{i=1}^{n}\|\phi(x_i; W) - c\|^2 + \frac{\lambda}{2}\|W\|_F^2$$

where $x_i$ is the feature vector, n is a number of training values, $\phi$ is an encoder network including the transformers and aggregation network, W are neural network parameters, c is a hypersphere in feature space, and $\lambda$ is a hyperparameter; and
performing a corrective action responsive to the health event to correct or mitigate a negative health effect of the health event.

19. The method of claim 18, wherein performing the corrective action includes an action selected from the group consisting of adjusting operation of a dialysis machine, adjusting dosage of an intravenously administered drug, and halting a treatment.

* * * * *